United States Patent [19]

Lachocki et al.

[11] Patent Number: 5,674,429
[45] Date of Patent: Oct. 7, 1997

[54] CHLOROISOCYANURIC ACID COMPOSITION HAVING REDUCED GAS EVOLUTION

[75] Inventors: Thomas M. Lachocki, Duluth; Presley K. Mitchell, Marietta; Oscar T. Ragin, Stone Mountain, all of Ga.

[73] Assignee: Bio-Lab, Inc., Decatur, Ga.

[21] Appl. No.: 441,382

[22] Filed: May 15, 1995

[51] Int. Cl.$^6$ .................. A62D 3/00; C02F 1/76
[52] U.S. Cl. .................. 252/186.28; 252/186.21; 252/186.35; 210/754
[58] Field of Search ............ 252/186.1, 186.21, 252/186.35, 186.28; 210/753, 754

[56] References Cited

U.S. PATENT DOCUMENTS

| | | | |
|---|---|---|---|
| 4,043,931 | 8/1977 | Jeffrey et al. | 252/93 |
| 4,350,666 | 9/1982 | Klutts | 422/263 |
| 4,460,490 | 7/1984 | Barford et al. | 252/92 |
| 4,594,091 | 6/1986 | Girvan | 71/67 |
| 4,738,728 | 4/1988 | Barford et al. | 134/34 |
| 5,021,186 | 6/1991 | Ota et al. | 252/186.35 |
| 5,131,938 | 7/1992 | Girvan | 514/64 |
| 5,178,787 | 1/1993 | Hung et al. | 252/90 |
| 5,205,955 | 4/1993 | Bunczk et al. | 252/102 |
| 5,330,676 | 7/1994 | Glen | 252/186.35 |
| 5,395,546 | 3/1995 | Hung et al. | 252/90 |
| 5,478,482 | 12/1995 | Jones et al. | 210/753 |
| 5,498,415 | 3/1996 | Jones | 424/409 |

FOREIGN PATENT DOCUMENTS

WO 93/04582  3/1993  WIPO.

OTHER PUBLICATIONS

OxyChem Material Safety Data Sheet, Apr. 23, 1993.

*Primary Examiner*—Shean C. Wu
*Attorney, Agent, or Firm*—Woodard, Emhardt, Naughton, Moriarty & McNett

[57] ABSTRACT

Disclosed are trichloroisocyanuric acid compositions that have improved algicidal and/or fungicidal properties yet are relatively safe and non-corrosive. The compositions preferably contain between about 50% and about 95% TCCA, between about 0.5% and about 7% glycoluril, between about 2% and about 40% alum, and between about 2% and about 40% borax. The compositions generate substantially less chlorine gas than would be expected from the teachings of the prior art, especially when wet. The inventive compositions are therefore less toxic and less corrosive.

24 Claims, No Drawings

CHLOROISOCYANURIC ACID COMPOSITION HAVING REDUCED GAS EVOLUTION

FIELD OF THE INVENTION

The present invention relates generally to sanitizing tablets for use in water systems, and more particularly to sanitizing tablets of chloroisocyanuric acid that are safer and easier to use due to their reduced propensity to generate hazardous and corrosive chlorine gas.

BACKGROUND TO THE INVENTION

Chloroisocyanuric acids such as trichloroisocyanuric acid ("TCCA") have long been used as sanitizers for water systems such as swimming pools, spas, etc. One drawback to this use however, is that chloroisocyanuric acids generate chlorine or chlorine-containing gases that are hazardous to human health and corrosive to water treatment equipment. Corrosive chlorine gas also adversely affects the packaging used to store the chloroisocyanuric acid, so that storage problems associated with the decomposition of the sanitizer are compounded by storage problems associated with the corrosion of the packaging itself.

The evolution of chlorine gas from TCCA-containing compositions is especially pronounced when the TCCA is wet, such as when the TCCA is formulated into solid pucks or tablets that are placed into water to sanitize the system. For example, in swimming pools it is common to use chemical feeder systems that rely on pumps to recirculate the treated water throughout the system. In many cases, the pump is turned off at night, and when the attendant opens the feeder in the morning the initial shock from built-up chlorine gas may be strong enough to make the attendant sick or disoriented. These problems are well known to the swimming pool chemical industry, and sanitizers that have a reduced level of chlorine gas evolution have long been sought.

It is also known that boron derivatives such as sodium tetraborate (borax) provide beneficial algicidal and fungicidal properties to water. Unfortunately however, boron derivatives are known to promote the undesirable chlorine gas evolution from TCCA as described above. For example, U.S. Pat. No. 5,021,186 to Ota et al. shows that compositions comprising sodium tetraborate (9 g) and TCCA (21 g) generate 6.3 mg chlorine gas, compared to the 0.31 mg gas generated by a like amount of TCCA alone.

Finally, it is known that in some situations aluminum sulfates improve the stability of chloroisocyanuric acids and correspondingly reduce the evolution of chlorine-containing gas from such compositions. The benefits of adding alum to TCCA are limited however, and are not believed to be enhanced by adding gas-generating compounds such as boron derivatives to the alum/TCCA compositions. In fact, the contrary expectation has prevailed in the art, with skilled artisans believing that adding boron derivatives to the alum/TCCA compositions would result in unsatisfactory levels of chlorine gas generation.

In spite of the known disadvantages of using chloroisocyanuric acid and borax in water treatment systems, a need continues for trichloroisocyanuric acid compositions that take advantage of the beneficial algicidal and/or fungicidal properties of borax yet are relatively safe and non-corrosive. The present invention addresses that need.

SUMMARY OF THE INVENTION

Briefly describing the present invention there are provided trichloroisocyanuric acid compositions that have improved algicidal and/or fungicidal properties yet are relatively safe and non-corrosive. The compositions contain 30% to 98% TCCA, 0.2% to 15% glycoluril, 1% to 50% alum, and 1% to 50% borax. More preferably the compositions contain between about 50% and about 95% TCCA, between about 0.5% and about 7% glycoluril, between about 2% and about 40% alum, and between about 2% and about 40% borax.

The compositions generate substantially less chlorine gas than would be expected from the teachings of the prior art, especially when wet. The inventive compositions are therefore less toxic and less corrosive.

One object of the present invention is to provide trichloroisocyanuric acid compositions that have improved algicidal and/or fungicidal properties yet are relatively safe and non-corrosive.

Further objects and advantages of the present invention will be apparent from the following description.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the described embodiments, and such further applications of the principles of the invention as described herein, being contemplated as would normally occur to one skilled in the art to which the invention pertains.

As indicated above, the present invention relates generally to sanitizing tablets of trichloroisocyanuric acid. The inventive compositions additionally contain aluminum sulfate and borax hydrate to provide additional algicidal and/or fungicidal properties, yet do not generate the expected levels of chlorine gas and are therefore relatively safe and non-corrosive. The compositions optionally contain glycoluril, and other components such as tabletting aids, mold release agents, corrosion inhibitors, scale inhibitors and/or dyes may be used. The relative proportions of the various components, as well as potential substitutions therefore, are described below. Representative examples of the preparation and use of the compositions are also presented.

As to the chloroisocyanuric acid, trichloroisocyanuric acid ("TCCA" or "trichlor") is preferred although dichloroisocyanuric acid may be used. Both of these chemicals are staple chemicals which are commercially available. In this patent document the names trichloroisocyanuric acid, TCCA and trichlor are used interchangeably, as is the more proper chemical name, trichloro-s-triazinetrione.

The concentration of trichlor in the total formula is generally between about 30 and 98%. Preferably trichlor is present in an amount of between about 50% and 95%; most preferably between about 65% and 90% of the total formula mass. In another aspect of the present invention TCCA is optionally replaced in part or entirely with other slow dissolving halogen sanitizers like 1-bromo-3-chloro-5,5-dimethylhydantoin, 1,3-dichloro-5,5-dimethylhydantoin or other halogenated and/or alkylated hydantoins.

The aluminum sulfate (alum) of the present invention commonly is provided having any of a variety of different equivalent amounts of hydrated water. Any hydrate is acceptable for use in the invention; preferably alum having from 2 to 20 equivalents of water per mole of aluminum sulfate is used. In alternative embodiments of the invention the aluminum sulfate is a hydrated potassium alum, or hydrated sodium alum.

The aluminum sulfate concentration can be varied from 1 to 50 or preferably from 2 to 40 percent of the total formula mass. In the most preferred embodiment the aluminum sulfate is present in an amount of between about 5% and about 30% of the total composition.

The boron-containing component is preferably provided as a borax hydrate, a product which is commercially available with a variety of different equivalent amounts of hydrated water. Borax hydrates that contain from 3 to 18 equivalents of water, or preferably from 4 to 14 equivalents of water per mole of borax, are most effectively used. Additionally, the borax can be partially or totally replaced with other boron-containing compounds such as boric acid or other borax oxygen oligomers.

The sodium tetraborate (borax) concentration can be varied from 1 to 50 or preferably from 2 to 40 percent of the total formula mass. In the most preferred embodiment the borax is present in the amount of between about 4% and about 20% of the total composition.

The inclusion of glycoluril in the compositions of the present invention is optional. In the preferred embodiments however, glycoluril is included in the formulation. The glycoluril may be substituted or unsubstituted, and is most preferably of the structure:

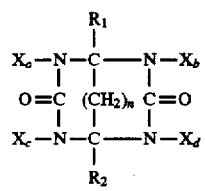

wherein $R_1$ and $R_2$ are each selected from the group consisting of hydrogen, lower alkyl groups of from 1–4 carbon atoms and phenyl; each $X_i$ (where i=a, b, c or d) is selected from the group consisting of hydrogen, chlorine and bromine; and n is either 0 or 1. As used herein, the term "glycoluril" includes all forms of glycoluril falling within the above formula. The term "unsubstituted glycoluril" refers solely to glycoluril according to the foregoing formula in which each of $R_1$, $R_2$ and $X_i$ is hydrogen.

The glycoluril is preferably included in the amount of between about 0.2 and about 15 percent. Preferably from 0.5 to 7% glycoluril is used, most preferably about 1% to about 5%.

The average glycoluril particle size is typically less than 500 microns. Dimethylhydantoin ("DMH") or other molecules that contain imide and amide functional groups or these molecules' halogenated analogues can be used to either partially or totally replace the glycoluril. The particle sizes of the other mixture components typically are smaller than 2.0 millimeters.

The compositions of the present invention are preferably provided as a solid compressed product, and may be of virtually any size or shape. Most preferably, the compressed product is shaped as a solid tablet, stick or puck which is easily accommodated by standard swimming pool skimmer baskets, chemical feeders or floating release devices. For other uses, such as in hot tubs, spas, toilet bowls and industrial applications, different sizes and/or shapes may be preferred.

As previously indicated, additional components such as binders, tabletting aids, mold release agents, corrosion inhibitors, scale inhibitors or dyes may be incorporated into the tablets or pucks. The selection of such components is within the capability of those skilled in the art.

Reference will now be made to specific examples using the processes described above. It is to be understood that the examples are provided to more completely describe preferred embodiments, and that no limitation to the scope of the invention is intended thereby.

EXAMPLES 1–16

General Procedure for examples 1–16: Blended products were prepared by weighing the appropriate amounts of each constituent into a container. The container was then thoroughly mixed. A one gram sample of the test formula contained in a metal cylinder (0.75 inch diameter) was compressed with 400 lbs. of force for 15 minutes. In some examples 9–16, a similar wafer was prepared and 0.10 ml of water would be sprayed on the wafer to determine the impact of water on the amount of gaseous oxidant released from the test formulas.

The small wafer that resulted was transferred to an 8 ounce container. A small beaker with 5 ml of a potassium iodide solution (15%) was placed beside the wafer in the container. The container was sealed and placed in an oven that was heated (50°–70° C.). After about 16 hours, an aliquot of the KI solution was removed and titrated with a 0.100 N solution of sodium thiosulfate. The volume of thiosulfate reagent used in the titration was recorded. The volume of thiosulfate used in this titration is proportional to the amount of gaseous oxidant (chlorine, chloramines, etc.) released from the sample.

As can be seen from the tables below, compositions comprising TCCA, borax and alum generate significantly less chlorine gas than would be expected from the data relating to TCCA, alum and borax alone. In particular, for the examples (1–8) where no water is added to the composition, it can be seen that whereas compositions comprising 25% alum generate chlorine gas requiring 0.53 ml of $Na_2S_2O_3$ to titrate, and whereas compositions comprising 25% borax generate chlorine gas requiring 5.44 ml of $Na_2S_2O_3$ to titrate, compositions comprising 12.5% borax and 12.5% alum generate chlorine gas requiring only 1.00 ml of $Na_2S_2O_3$ to titrate—far less than the weighted average of the gas generated by the two components. This result is unexpected, and is surprising in view of the teaching of the prior art.

Similarly, whereas compositions comprising 12.5% alum generate chlorine gas requiring 0.80 ml of $Na_2S_2O_3$ to titrate, and whereas compositions comprising 12.5% borax generate chlorine gas requiring 3.23 ml of $Na_2S_2O_3$ to titrate, compositions comprising 12.5% borax and 12.5% alum generate chlorine gas requiring only 1.00 ml of $Na_2S_2O_3$ to titrate—far less than the additive amount of the two components.

In the examples (9–16) where water is added to the composition the result is equally surprising. In particular, it can be seen that whereas compositions comprising 25% alum generate chlorine gas requiring 0.49 ml of $Na_2S_2O_3$ to titrate, and whereas compositions comprising 25% borax generate chlorine gas requiring 2.92 ml of $Na_2S_2O_3$ to titrate, compositions comprising 12.5% borax and 12.5% alum generate chlorine gas requiring only 0.97 ml of $Na_2S_2O_3$ to titrate—far less than the weighted average of the gas generated by the two components. Similarly, whereas compositions comprising 12.5% alum generate chlorine gas requiring 0.57 ml of $Na_2S_2O_3$ to titrate, and whereas compositions comprising 12.5% borax generate chlorine gas requiring 3.00 ml of $Na_2S_2O_3$ to titrate, compositions comprising 12.5% borax and 12.5% alum generate chlorine gas requiring only 0.97 ml of $Na_2S_2O_3$ to titrate—far less than the additive amount of the two components.

The Tables below summarize the data.

EXAMPLES 1–8

Using the general procedure above these formulas were mixed, wafers were prepared and the amount of gaseous oxidant released were quantified.

in this titration is proportional to the amount of gaseous oxidant (chlorine, chloramines, etc.) released from the sample.

Again the results show an unexpected and surprising result when both borax and alum are included in the TCCA composition. In particular, whereas compositions comprising 25% alum generate chlorine gas requiring 0.73 ml of $Na_2S_2O_3$ to titrate, and whereas compositions comprising 25% borax generate chlorine gas requiring 2.05 ml of $Na_2S_2O_3$ to titrate, compositions comprising 12.5% borax and 12.5% alum generate chlorine gas requiring only 0.68 ml of $Na_2S_2O_3$ to titrate—less than the weighted average of the gas generated by the two components, and even less than the gas generated by the TCCA/alum composition alone. Similarly, whereas compositions comprising 12.5% alum

| Example | 1 | 2 | 3 | 4 | 5 | 6 | 7 | 8 reference |
|---|---|---|---|---|---|---|---|---|
| Notebook # | 1035-12-1 | −2 | −3 | −4 | −5 | −6 | −7 | −8 reference |
| % Trichloro | 70 | 70 | 95 | 70 | 82.5 | 82.5 | 78.3 | 100 |
| % glycoluril | 4 | 4 | 4 | 4 | 4 | 4 | 4 | 0 |
| % DMH | 1 | 1 | 1 | 1 | 1 | 1 | 1 | 0 |
| % Alum | 25 | 0 | 0 | 12.5 | 0 | 12.5 | 8.3 | 0 |
| % Borax | 0 | 25 | 0 | 12.5 | 12.5 | 0 | 8.3 | 0 |
| Volume $Na_2S_2O_3$, ml | 0.53 | 5.44 | 0.75 | 1.00 | 3.23 | 0.80 | 2.25 | 0.28 |
| Added Chemical | | | | None | | | | |
| wt % added | | | | Not Applicable | | | | |

EXAMPLES 9–16

Using the general procedure above, these formulas were mixed, wafers were prepared, the wafer was contaminated with 0.1 ml of water, and the amount of gaseous oxidant released was quantified.

| Example | 9 | 10 | 11 | 12 | 13 | 14 | 15 | 16 reference |
|---|---|---|---|---|---|---|---|---|
| Notebook # | 1035-13-1 | −2 | −3 | −4 | −5 | −6 | −7 | −8 reference |
| % Trichloro | 70 | 70 | 95 | 70 | 82.5 | 82.5 | 78.3 | 100 |
| % glycoluril | 4 | 4 | 4 | 4 | 4 | 4 | 4 | 0 |
| % DMH | 1 | 1 | 1 | 1 | 1 | 1 | 1 | 0 |
| % Alum | 25 | 0 | 0 | 12.5 | 0 | 12.5 | 8.3 | 0 |
| % Borax | 0 | 25 | 0 | 12.5 | 12.5 | 0 | 8.3 | 0 |
| Added Chemical | | | | | Water | | | |
| Wt % added | | | | | 0.01% | | | |
| Volume $Na_2S_2O_3$, ml | 0.49 | 2.92 | 3.08 | 0.97 | 3.00 | 0.57 | 1.98 | 2.54 |

EXAMPLES 17–24

General Procedure for examples 17–24: Blended products were prepared by weighing the appropriate amounts of each constituent into a container, the container was then thoroughly mixed in a Vee-type blender.

A 100 g sample of the test formula was transferred to a three inch diameter metal dye. The formula was compressed for 0.2 minutes with 21 tons of pressure.

The puck that resulted was transferred to an 8 ounce container. A small beaker with 10 ml of a potassium iodide solution (15%) was placed on top of the puck in the container. The container was sealed and placed in an oven (50°–70° C.). After about 16 hours, an aliquot of the KI solution was removed and titrated with a 0.100 N solution of sodium thiosulfate. The volume of thiosulfate reagent used in the titration was recorded. The volume of thiosulfate used generate chlorine gas requiring 1.10 ml of $Na_2S_2O_3$ to titrate, and whereas compositions comprising 12.5% borax generate chlorine gas requiring 1.73 ml of $Na_2S_2O_3$ to titrate, compositions comprising 12.5% borax and 12.5% alum generate chlorine gas requiring only 0.68 ml of $Na_2S_2O_3$ to titrate—again less than the additive amount of the two components and less than either TCCA or TCCA/ alum alone.

A Table summarizing the data is provided below.

EXAMPLES 17–24

Using the General Procedure 2, pucks with the composition shown below were prepared and the amount of chlorine-gas released was quantified.

| Example | 17 | 18 | 19 | 20 | 21 | 22 | 23 | 24 reference |
|---|---|---|---|---|---|---|---|---|
| Notebook # | 1035-23-1 | -2 | -3 | -4 | -5 | -6 | -7 | -8 reference |
| % Trichloro | 70 | 70 | 95 | 70 | 82.5 | 82.5 | 78.3 | 100 |
| % glycoluril | 4 | 4 | 4 | 4 | 4 | 4 | 4 | 0 |
| % DMH | 1 | 1 | 1 | 1 | 1 | 1 | 1 | 0 |
| % Alum | 25 | 0 | 0 | 12.5 | 0 | 12.5 | 8.3 | 0 |
| % Borax | 0 | 25 | 0 | 12.5 | 12.5 | 0 | 8.3 | 0 |
| Volume $Na_2S_2O_3$, ml | 0.73 | 2.05 | 2.64 | 0.68 | 1.73 | 1.10 | 1.08 | 3.36 |

EXAMPLES 25–29

Several samples were subjected to the DOT Oxidizer Test, in accordance with Section 173, Apendix F of the Code of Federal Regulations, Title 49 by the procedure described below.

Thirty grams of a mixture of sample to sawdust (softwood, mesh 200), containing 1 to 1 and 4 to 1 ratios by mass, were prepared, placed in conical piles, and ignited by means of a wire heated to 1,000° C. until first signs of combustion were noticed or until it was clear that the pile could not be ignited. This was repeated three times for each mixing ratio.

Similar tests were performed using ammonium persulfate, potassium perchlorate, and potassium perbromate if needed, each in 1 to 1 ratios with wood flour as reference materials. These tests were repeated two more times for a total of three trials per reference material. Based on the sample burn time relative to the reference materials, the sample was classified into a packaging groups based on their relative hazard.

The relative oxidative hazard progresses in the order shown: Packaging Group I>Packaging Group II>Packaging Group III>Not Considered an Oxidizer The room conditions for the test were 68° F. and 35–45% relative humidity. The results of the tests are shown in the Table below.

Into a container, eight test formula tablets (approx. 18 grams each) were stacked. Pool water was added to the container to completely submerge the tablets. The ratio of sample to water was similar to that encountered in a typical chlorinator. The container was then sealed with a stopper that allows headspace gases to be purged. The assembly was connected to a series of two gas scrubbers. Each scrubber unit contained 50 mL of 15% potassium iodide solution. A regulated flow of air was passed through the assembly to transfer the headspace gases into the scrubbers. The air flow was measured at the output of the test system to ensure that the flow rates were constant for each example. After about 4 hours, the flow was stopped and the KI solution for the two scrubbers was combined. The solution was titrated with a 0.0100 N sodium thiosulfate solution. The volume of thiosulfate used for each titration is proportional to the amount of gaseous oxidant (chlorine, chloramines, etc.) released from the sample. The concentration of chlorine that corresponds to the volume of thiosulfate used was calculated.

EXAMPLES 30–31

Using the general procedure above, the formulas were mixed, tablets were prepared and the amount of gaseous oxidant released was quantified. The results are shown in the Table below.

| Example | 24 ref. | 25 | 26 | 27 | 28 ref. | 29 |
|---|---|---|---|---|---|---|
| Notebook # | xxx | 1030-123 | 1030-125 | 1030-127 | xxx | xxx |
| % Trichloro | 100 | 72.1 | 72.0 | 72.3 | 97.5 | 92.5 |
| % glycoluril | 0 | 2.9 | 3.2 | 2.8 | 2.5 | 2.5 |
| % Alum | 0 | 18.0 | 18.0 | 18.1 | 0 | 0 |
| % Borax | 0 | 6.8 | 6.8 | 6.6 | 0 | 5.0 |
| % Boric Acid | 0 | 0.1 | 0.1 | 0.2 | 0 | 0 |
| % Lazurite Dye | 0 | 0 | 0 | 0.1 | 0 | 0 |
| Packaging Group Classification | Group II | Not An Oxidizer | Not An Oxidizer | Group III | Group II | Group II |

It can be seen from examples 25–29 that the inclusion of alum and borax in TCCA-containing compositions makes the compositions safer with respect to its packaging hazard.

EXAMPLES 30–33

GENERAL PROCEDURE

Blended products were prepared by weighing the appropriate amounts of each constituent into a container. The container was then thoroughly mixed. Approximately 18 grams of the test formula were compressed under conditions to produce one inch diameter tablets with a crush strength comparable to commercial trichloro tablets.

| Example | Volume of $Na_2S_2O_3$ (ml) | Conc. as Chlorine (mg/L) | Total Sample Mass (g) | Initial pH | Final pH |
|---|---|---|---|---|---|
| 100% TCCA | 27.05 | 96 | 144.08 | 6.5 | 2.6 |
| 7% Borax, 18% Alum, 73% TCCA | 7.19 | 25 | 144.11 | 6.5 | 3.7 |

The amount of chlorine released by the test formula tablets was substantially lower than one would predict based on the relative TCCA concentrations of the test substances.

EXAMPLES 32–33

Using the general procedure above, these formulas were mixed and tablets were prepared. The pH of the pool water used was adjusted to 9.5. The amount of gaseous oxidant released was quantified, as shown in the Table below.

| Example | Volume of $Na_2S_2O_3$ (ml) | Conc. as Chlorine (mg/L) | Total Sample Mass (g) | Initial pH | Final pH |
|---|---|---|---|---|---|
| 100% TCCA | 32.97 | 120 | 144.44 | 9.5 | 2.8 |
| 7% Borax, 18% Alum, 73% TCCA | 3.06 | 11 | 143.31 | 9.5 | 3.7 |

In can be seen from the foregoing that the amount of chlorine released by the test formula tablets was substantially lower than one would predict based on the relative TCCA concentrations of the test substances.

While the invention has been illustrated and described in detail in the drawing and foregoing description, the same is to be considered as illustrative and not restrictive in character, it being understood that only the preferred embodiment has been shown and described and that all changes and modifications that come within the spirit of the invention are desired to be protected.

We claim:

1. A sanitizing and clarifying product with a reduced propensity to generate chlorine gas, comprising:
   (a) between about 30% and about 98% trichloro-s-triazinetrione;
   (b) between about 1% and about 50% sodium tetraborate; and
   (c) between about 1% and about 50% aluminum sulfate.

2. The sanitizing and clarifying product of claim 1 wherein the product comprises from about 50% to about 95% trichloro-s-triazinetrione.

3. The sanitizing and clarifying product of claim 2 wherein the product comprises from about 65% to about 90% trichloro-s-triazinetrione.

4. The sanitizing and clarifying product of claim 1 wherein the product comprises from about 2% to about 40% sodium tetraborate.

5. The sanitizing and clarifying product of claim 4 wherein the product comprises from about 4% to about 20% sodium tetraborate.

6. The sanitizing and clarifying product of claim 1 wherein the product comprises from about 2% to about 40% aluminum sulfate.

7. The sanitizing and clarifying product of claim 6 wherein the product comprises from about 5% to about 30% aluminum sulfate.

8. The sanitizing and clarifying product of claim 1, and further comprising between about 0.5% and about 7% glycoluril.

9. The sanitizing and clarifying product of claim 8 wherein the product comprises from about 0.5% to about 7% glycoluril.

10. The sanitizing and clarifying product of claim 9 wherein the product comprises about 1% to about 5% glycoluril.

11. The sanitizing and clarifying product of claim 1 wherein the product further comprises boric acid.

12. The sanitizing and clarifying product of claim 1 wherein the product further comprises a dye.

13. A method of clarifying and sanitizing water while minimizing the generation of undesirable chlorine gas, the method comprising adding to the water a sanitizing and clarifying product comprising:
   (a) about 30% to about 98% trichloro-s-triazinetrione;
   (b) about 1% to about 50% sodium tetraborate; and
   (c) about 1% to about 50% aluminum sulfate.

14. The method of claim 13 wherein the sanitizing and clarifying product comprises from about 50% to about 95% trichloro-s-triazinetrione.

15. The method of claim 14 wherein the sanitizing and clarifying product comprises from about 65% to about 90% trichloro-s-triazinetrione.

16. The method of claim 13 wherein the sanitizing and clarifying product comprises from about 2% to about 40% sodium tetraborate.

17. The method of claim 16 wherein the sanitizing and clarifying product comprises from about 4% to about 20% sodium tetraborate.

18. The method of claim 13 wherein the sanitizing and clarifying product comprises from about 2% to about 40% aluminum sulfate.

19. The method of claim 18 wherein the sanitizing and clarifying product comprises from about 5% to about 30% aluminum sulfate.

20. The method of claim 13 wherein the sanitizing and clarifying product further comprises from about 0.2% to about 15% glycoluril.

21. The method of claim 20 wherein the sanitizing and clarifying product comprises from about 0.5% to about 7% glycoluril.

22. The method of claim 21 wherein the sanitizing and clarifying product comprises about 1% to about 5% glycoluril.

23. The method of claim 13 wherein the sanitizing and clarifying product further comprises boric acid.

24. The method of claim 13 wherein the sanitizing and clarifying product further comprises a dye.

* * * * *

UNITED STATES PATENT AND TRADEMARK OFFICE
CERTIFICATE OF CORRECTION

PATENT NO. : 5,674,429
DATED : October 7, 1997
INVENTOR(S) : Thomas M. Lachocki et al.

It is certified that error appears in the above-identified patent and that said Letters Patent is hereby corrected as shown below:

In col. 2, lines 45 and 46, please change "diehloroisocyanuric" to --dichloroisocyanuric--.

Signed and Sealed this

Twenty-fourth Day of March, 1998

Attest:

BRUCE LEHMAN

*Attesting Officer*        *Commissioner of Patents and Trademarks*